United States Patent

Kysela et al.

Patent Number: 5,142,092
Date of Patent: Aug. 25, 1992

[54] FLUORINE-CONTAINING ACETOPHENONES OPTIONALLY HALOGENATED ON THE CH₃-GROUP AND THEIR PRECURSER FLUORINE-CONTAINING BENZONITRILES

[75] Inventors: Ernst Kysela, Bergisch Gladbach; Bernd Baasner, Leverkusen; Klaus Schaller, Wuppertal, all of Fed. Rep. of Germany

[73] Assignee: Bayer Aktiengesellschaft, Leverkusen, Fed. Rep. of Germany

[21] Appl. No.: 739,738

[22] Filed: Jul. 30, 1991

Related U.S. Application Data

[63] Continuation of Ser. No. 421,442, Oct. 13, 1989, abandoned.

[30] Foreign Application Priority Data

Oct. 24, 1988 [DE] Fed. Rep. of Germany ....... 3836159

[51] Int. Cl.⁵ .................... C07C 47/55; C07C 255/50
[52] U.S. Cl. .................................... 558/423; 558/425; 568/335; 568/337
[58] Field of Search ................. 558/423, 425; 568/335

[56] References Cited

U.S. PATENT DOCUMENTS

| | | | |
|---|---|---|---|
| 3,184,379 | 5/1965 | Lukes et al. ............... | 568/335 |
| 3,267,110 | 8/1966 | Pachter et al. ............ | 546/328 |
| 3,916,007 | 10/1975 | Klauke ..................... | 71/105 X |
| 4,329,342 | 5/1982 | Heeres et al. ............. | 568/335 |
| 4,446,078 | 5/1984 | Desbois ..................... | 564/329 X |

FOREIGN PATENT DOCUMENTS

| | | |
|---|---|---|
| 0079154 | 5/1983 | European Pat. Off. . |
| 0085265 | 8/1983 | European Pat. Off. . |
| 2550262 | 5/1977 | Fed. Rep. of Germany . |
| 3529259 | 2/1987 | Fed. Rep. of Germany ...... 568/335 |
| 1657806 | 5/1969 | France . |
| 2177093 | 11/1973 | France . |
| 1187174 | 4/1970 | United Kingdom . |

Primary Examiner—Mary C. Lee
Assistant Examiner—Jacqueline Haley
Attorney, Agent, or Firm—Sprung Horn Kramer & Woods

[57] ABSTRACT

Fluorine-containing acetophenones, optionally halogenated on the CH₃ group, of the formula

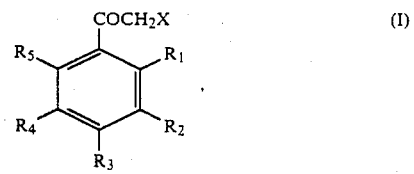

in which
X represents hydrogen, chlorine or bromine and the radicals $R_1$ to $R_5$ have the following meaning,
 a) $R_1$ and $R_4$ denote fluorine, $R_2$ and $R_5$ denote chlorine and $R_3$ denotes $CF_3$, or
 b) $R_1$, $R_3$ and $R_4$ denote fluorine and $R_2$ and $R_5$ denote hydrogen, or
 c) $R_1$, $R_4$ and $R_5$ denote hydrogen, $R_2$ denotes chlorine and $R_3$ denotes $CF_3$, or
 d) $R_1$, $R_4$ and $R_5$ denote hydrogen, $R_2$ denotes chlorine and $R_3$ denotes $OCF_3$, or
 e) $R_1$, $R_4$ and $R_5$ denote hydrogen and $R_2$ and $R_3$ denote $CF_3$, or
 f) $R_1$ denotes chlorine, $R_2$ denotes $CF_3$ and $R_3$, $R_4$ and $R_5$ denote hydrogen, or
 g) $R_1$ denotes chlorine, $R_2$, $R_3$ and $R_4$ denote hydrogen and $R_5$ denotes $CF_3$, or
 h) $R_1$ denotes chlorine, $R_2$, $R_4$ and $R_5$ denote hydrogen and $R_3$ denotes $CF_3$ and a process for their preparation from the corresponding fluorinated benzonitriles or benzyl halides by reaction with an organomagnesium compound capable of introducing methyl groups and subsequent hydrolysis, if appropriate followed by a chlorination or bromination.

2 Claims, No Drawings

FLUORINE-CONTAINING ACETOPHENONES OPTIONALLY HALOGENATED ON THE CH₃-GROUP AND THEIR PRECURSER FLUORINE-CONTAINING BENZONITRILES

This application is a continuation, of application Ser. No. 421,442, filed Oct. 13, 1989, now abandoned.

The present invention relates to new fluorine-containing acetophenones, optionally halogenated on the CH₃ group, of the formula

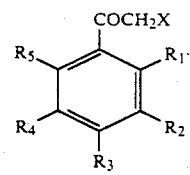

in which

X represents hydrogen, chlorine or bromine and the radicals $R_1$ to $R_5$ have the following meaning, a) $R_1$ and $R_4$ denote fluorine, $R_2$ and $R_5$ denote chlorine and $R_3$ denotes $CF_3$, or
b) $R_1$, $R_3$ and $R_4$ denote fluorine and $R_2$ and $R_5$ denote hydrogen, or
c) $R_1$, $R_4$ and $R_5$ denote hydrogen, $R_2$ denotes chlorine and $R_3$ denotes $CF_3$, or
d) $R_1$, $R_4$ and $R_5$ denote hydrogen, $R_2$ denotes chlorine and $R_3$ denotes $OCF_3$, or
e) $R_1$, $R_4$ and $R_5$ denote hydrogen and $R_2$ and $R_3$ denote $CF_3$, or
f) $R_1$ denotes chlorine, $R_2$ denotes $CF_3$ and $R_3$, $R_4$ and $R_5$ denote hydrogen, or
g) $R_1$ denotes chlorine, $R_2$, $R_3$ and $R_4$ denote hydrogen and $R_5$ denotes $CF_3$, or
h) $R_1$ denotes chlorine, $R_2$, $R_4$ and $R_5$ denote hydrogen and $R_3$ denotes $CF_3$.

Fluorine-containing acetophenones of the formula (I) in which X = hydrogen and the substituents have the meanings indicated under c) to h) are preferred. Very particularly preferred fluorine-containing acetophenones of the formula (I) in which X = hydrogen are those in which the substituents have the meanings indicated under f) to h), i.e. 2-chloro-3-trifluoromethyl-acetophenone, 2-chloro-4-trifluoromethyl-acetophenone and 2-chloro-6- trifluoromethyl-acetophenone.

Of the acetophenones halogenated on the CH₃ group of the formula (I) in which X = chlorine or bromine, the corresponding compounds are preferred. Very particularly preferred here are 2-chloro-3-trifluoromethylphenacyl bromide and chloride, 2-chloro-4-trifluoromethyl-phenacyl bromide and chloride and 2-chloro-6-trifluoromethylphenacyl bromide and chloride.

The present invention also relates to a process for the preparation of fluorine-containing acetophenones of the formula (I), which are optionally halogenated on the CH group, which is characterized in that, for the preparation of compounds of the formula (I) in which X = hydrogen, a fluorinated benzoic acid derivative of the formula (II)

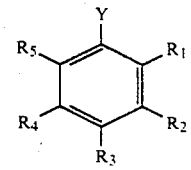

in which $R_1$ to $R_5$ have the meaning indicated in formula (I) and

Y represents a nitrile group or an acid halide group, is reacted with an organomagnesium compound capable of introducing methyl groups and a hydrolysis is then carried out and, for the preparation of compounds of the formula (I) in which X = chlorine or bromine, the product is further subsequently reacted at -20 to +80° C. with a chlorinating or brominating agent.

For use in the process according to the invention, those fluorinated benzoic acid derivatives of the formula (II) are preferred in which R to R: have the meanings indicated in formula (I) under c) to h). Particularly preferred are fluorinated benzoic acid derivatives in which $R_1$ to $R_5$ have the meanings indicated in formula (I) under f) to h).

If Y represents an acid halide group in formula (II), it is preferably an acid fluoride or acid chloride group (COF or COCl), in particular an acid fluoride group (COF).

In formula (II), Y preferably represents a nitrile group.

Fluorinated benzoic acid derivatives of the formula (II), in which Y represents an acid halide group, are known (see, for example, DE-OS (German Published Specification) 3,621,707).

Some of the fluorinated benzoic acid derivatives of the formula (II) in which X represents a nitrile group are known and some are new. New fluorinated benzonitriles are in particular those of the formula (IIa)

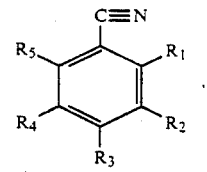

in which $R_1$, $R_4$ and $R_5$ represent hydrogen and $R_2$ and $R_3$ represent $CF_3$ or
$R_1$, $R_4$ and $R_5$ represent hydrogen, $R_2$ represents chlorine and $R_3$ represents $OCF_3$ or
$R_2$, $R_3$ and $R_4$ represent hydrogen, $R_1$ represents chlorine and $R_5$ represents $CF_3$.

The present invention therefore also relates to such new fluorinated benzonitriles of the formula (IIa). Possibilities for preparation of the new fluorinated benzonitriles are indicated in Examples 1a), 2a) and 2b) and 5a).

The organomagnesium compounds capable of introducing methyl groups may be, for example, methylmagnesium halides, in particular methylmagnesium bromide or methylmagnesium iodide, or ethoxymagnesium ethyl malonate.

The latter is, for example, accessible by reacting magnesium diethoxide with diethyl malonate and in this way replacing one ethoxy group of the magnesium diethoxide by an ethyl malonate group. Using ethoxymagnesium ethyl malonate, an ethyl malonate radical can be introduced onto the C atom in the radical Y of the fluorinated benzoic acid derivative of the formula (II), which radical is then converted to a methyl group on hydrolysis, by means of decarboxylation.

Relative to 1 mole of fluorinated benzoic acid derivative of the formula (II), for example, 0.8 to 3 moles of the particular organomagnesium compound can be employed. Preferably, this amount is 1 to 1.5 moles. The organomagnesium compound is in general used in dissolved form. Suitable solvents are, for example, ethers, in particular diethyl ether and tetrahydrofuran. In general, a solution of the particular organomagnesium compound is prepared separately and this is added to the compound of the formula (II), which may likewise be present in dissolved form. When using methylmagnesium halides, it may be advantageous to add a small amount of catalyst, for example a copper or iron salt.

The reaction of the benzoic acid derivative of the formula (II) with the organomagnesium compound can be carried out in a wide temperature range, for example between −60 and +100° C. The hydrolysis to be carried out after this reaction can be accomplished, for example, by pouring into or adding water and keeping at a temperature in the range from −10 to +40° C. for several hours. Preferably, acid is added, for example glacial acetic, hydrochloric or sulphuric acid. Carrying out the hydrolysis in the presence of a strong acid is particularly advantageous if ethoxymagnesium ethyl malonate has been employed as the organomagnesium compound.

The reaction mixture present after the hydrolysis can be worked up, for example, by separating off the organic phase therefrom and fractionally distilling the latter.

By means of the reaction of a benzoic acid derivative of the formula (II) with an organomagnesium compound capable of introducing methyl groups, with subsequent hydrolysis, fluorine-containing acetophenones of the formula (I) in which X = hydrogen are obtained. From these, acetophenones of the formula (I) which are halogenated on the CH3 group and in which X = chlorine or bromine can be obtained if they are reacted at -20 to 80° C. with a chlorinating or brominating agent. A suitable chlorinating agent is, for example, sulphuryl chloride (SO2Cl2; elemental bromine, for example, is suitable as a brominating agent.

In general, the chlorinating or brominating agent is employed in the stoichiometrically required amount or in excess, for example 1 to 1.2 moles per mole of starting material. Suitable reaction temperatures are those in the range from −20 to +80° C., in particular those from 0 to 40° C.

The chlorination or bromination can be carried out in the presence or absence of solvents. Preferably, it is carried out in the presence of inert organic solvents, for example methylene chloride or glacial acetic acid. Likewise, it is not absolutely necessary, but in general advantageous, to work in the presence of catalytic amounts of a strong, concentrated mineral acid. For example, sulphuric acid or hydrochloric acid are suitable here.

The end of the chlorination or bromination can be recognized by the cessation of the evolution of gas (hydrogen chloride or hydrogen bromide). The reaction mixture can then, for example, be worked up by mixing it with water or ice-water, extracting by shaking with an organic solvent, concentrating the organic extract and distilling the residue. If appropriate, a further purification can be carried out, for example by recrystallization, distillation or chromatography.

The new, fluorine-containing acetophenones of the formula (I) in which X chlorine or bromine can be converted by reaction with a thiourea derivative of the type

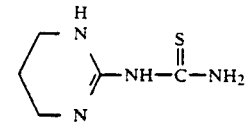

into substituted aminothiazoles of the type

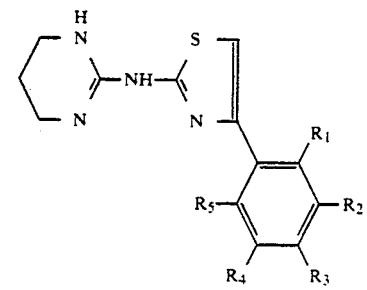

which are compounds which possess a good activity against pests, in particular fungi which are injurious to plants.

Substituted aminothiazoles of the type mentioned, their preparation and use are the subject of a separate patent application by the parent company.

It is to be regarded as surprising that the fluorinated acetophenones of the formula (I) according to the invention are accessible in good yields in the manner described, since in addition to the desired reaction, reactions with the activated halogen atoms bonded to the ring and hydrolysis of the CF3 groups bonded to the ring were to be expected.

EXAMPLES

EXAMPLE 1 a) 3,4-bistrifluoromethyl-benzonitrile 229 g (1 mole) of 3,4-bistrifluoromethyl-aniline were diazotized in a solution of 350 g of concentrated sulphuric acid in 1.25 l of water using 70 g of sodium nitrite in 140 ml of water. After the diazonium salt solution had become nitrite-free, it was added dropwise to a solution of 550 ml of water, 210 g of sodium cyanide, 10 g of copper (I) cyanide, 500 g of sodium hydrogen carbonate and 9 g of nickel sulphate ×7 H2O heated to 100° C. The product was isolated from the reaction mixture by steam distillation and subsequently distilled again. 152 g of product having a boiling point at 14 mbar of 85° C. and a melting point of 71° to 72° C. were obtained. This corresponds to a yield of 63% of theory.

b) 3,4-bistrifluoromethyl-acetophenone 119.5 g (0.5 mole) of 3,4-bistrifluoromethyl-benzonitrile were heated to reflux for 3 hours with 166 g (1 mole) of methylmagnesium iodide in 750 ml of benzene. After cooling to 0°, 500 ml of 6 N aqueous hydrochloric acid were allowed to flow in and the mixture was heated to reflux for a further 6 hours. The mixture was then cooled, and the organic phase was separated off and distilled. 123 g of product having a boiling point at 0.3 mbar of 71° to 73° C. were obtained. This corresponds to a yield of 48% of theory.

EXAMPLE 2 a) 3-Chloro-4-trifluoromethoxy-benzamide 242.5 g (1 mole) of 3-chloro-4-trifluoromethoxybenzoyl fluoride were allowed to drip into 500 ml of 25% strength by weight aqueous ammonia solution with ice cooling, the mixture was then stirred for a further 30 minutes and the precipitate which deposited was filtered off with suction. 227 g of product having a melting point of 98° C. were obtained. This corresponds to a crude yield of 95% of theory.

b) 3-Chloro-4-trifluoromethoxy-benzonitrile 750 ml of $SOCl_2$ were added to 239.5 g (1 mole) of 3-chloro-4-trifluoromethoxy-benzamide and the mixture was slowly heated (according to the evolution of gas) to 85° C. The mixture was then fractionally distilled and 189 g of product having a boiling point at 13 mbar of 96° C. and a melting point of 38° to 40° C. were obtained. This corresponds to a yield of 85% of theory.

c) 3-Chloro-4-trifluoromethoxy-acetophenone

Analogously to Example 1b), 221.5 g (1 mole) of 3-chloro-4-trifluoromethoxy-benzonitrile were reacted with methylmagnesium iodide and the reaction mixture was worked up correspondingly. 105.4 g of product having a boiling point at 0.1 mbar of 98° to 99° C. were obtained. This corresponds to a yield of 44% of theory.

EXAMPLE 3

3-Chloro-4-trifluoromethyl-acetophenone 226 g (1 mole) of 3-chloro-4-trifluoromethylbenzoyl fluoride were initially introduced into 500 ml of diethyl ether and, after addition of 3 g of $FeCl_3$, a Grignard solution prepared from 95 g (1 mole) of methyl bromide and 24.3 g of magnesium in 250 ml of diethyl ether was added dropwise at an internal temperature of −60° C. in the course of 4 hours. The mixture was kept at −60° C. for a further 24 hours, then warmed to 25° C. The reaction mixture was then poured into water, and the organic phase was separated off and fractionally distilled. 47.5 g of product having a boiling point at 0.2 mbar of 84° to 87° C. were obtained. This corresponds to a yield of 20% of theory.

EXAMPLE 4

2-Chloro-4-trifluoromethyl-acetophenone 81 g (0.358 mole) of 2-chloro-4-trifluoromethylbenzoyl chloride were reacted with methylmagnesium bromide analogously to Example 3 and the reaction mixture was worked up correspondingly. 35.2 g of product having a boiling point at 10 mbar of 80° to 81° C. were obtained. This corresponds to a yield of 44% of theory.

EXAMPLE 5 a) 2-Chloro-6-trifluoromethyl-benzonitrile 255 g (1 mole) of 2-chloro-6-trichloromethylbenzonitrile and 250 g of anhydrous hydrogen fluoride were heated in an autoclave at 140° C. for 4 hours. The hydrogen chloride formed was allowed to escape continuously at 25 bar. Excess hydrogen fluoride was then stripped off, the reaction residue was distilled, the distillate was collected in the boiling range from 80° to 142° C. at 15 mbar (180 g), 55 g of antimony trifluoride were added to this and the mixture was heated to 90° C. A small amount of chlorine was introduced into the reaction mixture at 90° C. in order to activate the antimony trifluoride. The mixture was then heated to 135° C. for a further hour. For working up, the reaction mixture was poured into water, and the organic phase was separated off and distilled. 138 g of product having a boiling point at 13 mbar of 112° to 113° C. and a melting point of 45° to 47° C. were obtained. This corresponds to a yield of 67% of theory.

b) 2-Chloro-6-trifluoromethyl-acetophenone 154 g (0.75 mole) of 2-chloro-6-trifluoromethylbenzonitrile were initially introduced into 375 ml of diethyl ether and, after addition of 1 g of CuCl, a Grignard solution prepared from 24.3 g of magnesium and 95 g (1 mole) of methyl bromide in 250 ml of diethyl ether was added dropwise at 28° to 30° C. in the course of 3 hours. The mixture was stirred at 28° to 30° C. for a further 5 hours. The reaction mixture was then poured into water, and the organic phase was separated off and distilled. 114 g of product having a boiling point at 0.3 mbar of 65° to 66° C. were obtained. This corresponds to a yield of 68% of theory.

EXAMPLE 6

2-Chloro-3-trifluoromethyl-acetophenone 193 g (0.94 mole) of 2-chloro-3-trifluoromethylbenzonitrile were reacted with methylmagnesium bromide analogously to Example 5 and the reaction mixture was worked up correspondingly. 94 g of product having a boiling point at 8 mbar of 90° to 91° C. were obtained. This corresponds to a yield of 45% of theory.

EXAMPLE 7

2,4,5-Trifluoro-acetophenone 194.5 g (1 mole) of 2,4,5-trifluoro-benzoyl chloride were initially introduced into 100 ml of diethyl ether and the mixture was heated to boiling under reflux. 1.1 mole of ethoxymagnesium ethyl malonate dissolved in 100 ml of ethanol and 125 ml of diethyl ether were then allowed to drip in in the course of 30 minutes and the mixture was stirred under reflux for a further 1 hour. After cooling, the reaction mixture was stirred into 500 ml of ice water and adjusted to a pH of 1 using concentrated sulphuric acid, and the organic material (345 g) was separated off. This organic material was dissolved in 300 ml of acetic acid and, after the addition of 37.5 ml of concentrated sulphuric acid, heated to reflux until the end of $CO_2$ evolution, which took 6 hours. The reaction mixture was then cooled and poured into water, and the organic phase was separated off and distilled. 83 g of product having a boiling point at 10 mbar of 63° to 64° C. were obtained. This corresponds to a yield of 47% of theory.

EXAMPLE 8

2,3,5,6-Tetrafluoro-4-trifluoromethyl-acetophenone 364 g (1 mole) of 2,3,5,6-tetrafluoro-4-tri-fluoromethyl-benzoyl fluoride were reacted with ethoxymagnesium ethyl malonate analogously to Example 7 and the reaction mixture was worked up correspondingly. 170 g of product having a boiling point at 60 mbar of 98° to 100° C. were obtained. This corresponds to a yield of 65% of theory.

EXAMPLES 9 to 15

General Working Procedure:

22.4 g (0.14 mole) of bromine dissolved in 50 ml of glacial acetic acid were added dropwise to 0.125 mole of a compound of the formula (I) in which X = hydrogen in 250 ml of glacial acetic acid, to which 1.25 ml of concentrated hydrochloric acid had been added, at room temperature (22° C.) in the course of 2 hours. The mixture was stirred for a further 2 hours at room temperature. The reaction mixture was then poured into 1 l of ice-water, the organic phase was separated off, the aqueous phase was extracted twice using 100 ml of dichloromethane each time, and the combined organic phases were washed twice with 150 ml of water each time and dried over magnesium sulphate. The solvent was then stripped off in a water pump vacuum. The details of the reactions carried out can be seen from Table 1, as can also the characterization of the products obtained carried out by recording the $^1$H-NMR spectrum (in CDCl$_3$ using tetramethylsilane as the internal standard) of the products obtained (in each case the δ value is indicated in ppm for the protons of the —CH$_2$—X group).

TABLE 1

| Ex. No. | Starting material obtained according to Example | Reaction product of the formula (I) in which X = bromine (substituents not mentioned are hydrogen) | Yield [% of theory] | Characterization |
|---|---|---|---|---|
| 9 | 1b | R$_2$ = R$_3$ = CF$_3$ | 83.8 | 5.30 |
| 10 | 2c | R$_2$ = Cl, R$_3$ = OCF$_3$ | 76.9 | 5.33 |
| 11 | 3 | R$_2$ = Cl, R$_3$ = CF$_3$ | 81.2 | 5.31 |
| 12 | 4 | R$_1$ = Cl, R$_3$ = CF$_3$ | 78.8 | 5.31 |
| 13 | 5b | R$_1$ = Cl, R$_5$ = CF$_3$ | 71 | 5.34 |
| 14 | 6 | R$_1$ = Cl, R$_2$ = CF$_3$ | 89 | 5.36 |
| 15 | 8 | R$_1$ = R$_2$ = R$_4$ = R$_5$ = F; R$_3$ = CF$_3$ | 94.3 | 5.20 |

EXAMPLE 16

40.8 g (0.3 mole) of sulphuryl chloride were added dropwise at room temperature (22° C.) to 48 g (0.275 mole) of 2,4,5-trifluoroacetophenone (obtained according to Example 6), dissolved in 400 ml of dichloromethane, and the mixture was stirred until the end of the evolution of hydrogen chloride (about 2 hours). 600 ml of water were then added to the reaction mixture, the organic phase was separated off, and this was washed until neutral with sodium hydrogen carbonate solution and dried over magnesium sulphate, and the solvent was stripped off in a water pump vacuum. 48.6 g of 2,4,5-trifluoro-phenacyl chloride were obtained as an oily residue, which corresponds to 84.5 % of theory. The characterization of the product carried out as in Examples 9 to 15 gave a δ value of 5.29 ppm.

What is claimed is:

1. A fluorinated benzonitrile of the formula

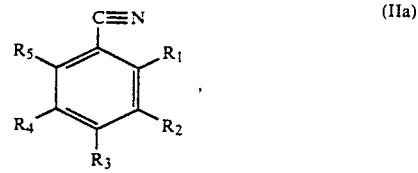

(IIa)

in which

R$_1$, R$_4$ and R$_5$ represent hydrogen, R$_2$ represents chlorine and R$_3$ represents OCF$_3$ or R$_2$, R$_3$ and R$_4$ represent hydrogen, R$_1$ represents chlorine and R$_5$ represents CF$_3$.

2. A fluorine-containing acetophenone selected from the group consisting of 2-chloro-3-trifluoromethyl-acetophenone, 2-chloro-4trifluoro-methyl-acetophenone, 2-chloro-6-trifluoromethyl-aceto-pheonone, 2-chloro-4trifluoromethyl-phenacyl bromide and chloride and 2-chloro-6trifluoromethylphenacyl bromide and chloride.

* * * * *

UNITED STATES PATENT AND TRADEMARK OFFICE
CERTIFICATE OF CORRECTION

PATENT NO. : 5,142,092
DATED : August 25, 1992
INVENTOR(S) : Kysela et al.

It is certified that error appears in the above-identified patent and that said Letters Patent is hereby corrected as shown below:

Col. 8, lines 42-45    After " 4 " insert -- - --; line 43 delete " aceto-pheonone " and substitute -- acetophenone --; after " acetophenone " insert -- 2-chloro-3-trifluoromethyl-phenacyl bromide and chloride -- ; line 44 after "4 " insert -- - --; line 45 after " 6 " insert -- - --.

Signed and Sealed this

First Day of March, 1994

Attest:

BRUCE LEHMAN

Attesting Officer        Commissioner of Patents and Trademarks